(12) United States Patent
Alcazar

(10) Patent No.: US 9,285,830 B2
(45) Date of Patent: Mar. 15, 2016

(54) INTERCHANGEABLE BATTERY WEARABLE DEVICE

(71) Applicant: Ross Dominique Diaz Alcazar, Aurora, IL (US)

(72) Inventor: Ross Dominique Diaz Alcazar, Aurora, IL (US)

( * ) Notice: Subject to any disclaimer, the term of this patent is extended or adjusted under 35 U.S.C. 154(b) by 272 days.

(21) Appl. No.: 14/067,642

(22) Filed: Oct. 30, 2013

(65) Prior Publication Data

US 2014/0218852 A1 Aug. 7, 2014

Related U.S. Application Data

(60) Provisional application No. 61/760,737, filed on Feb. 5, 2013.

(51) Int. Cl.
*G06F 11/30* (2006.01)
*G06F 1/16* (2006.01)
*A61B 5/00* (2006.01)

(52) U.S. Cl.
CPC .............. *G06F 1/163* (2013.01); *G06F 1/1635* (2013.01); *A61B 5/00* (2013.01)

(58) Field of Classification Search
CPC ....... G06F 1/163; G06F 3/16; G06F 3/04842; G06F 19/3406; G06F 19/322; G06F 1/3246; G06F 3/038; G06F 1/1635; H05K 1/028; H05K 1/0296; H05K 1/0306; H05K 1/038; H05K 1/0393; H05K 2201/0281; H05K 2201/058; H05K 2203/1157; H05K 3/103; H05K 3/105; A61B 5/681; A61B 5/01; A61B 5/1118; A61B 2562/0247; A61B 5/024; A61B 5/02427; A61B 2562/227; A61B 5/02405; A61B 5/18; A61B 5/6826
USPC ............ 361/679.03, 679.01, 679.21, 679.09, 361/679.26, 679.27, 679.4; 600/509, 508
See application file for complete search history.

(56) References Cited

U.S. PATENT DOCUMENTS

2005/0027200 A1* 2/2005 Chen .................. A61B 5/02438
600/509

* cited by examiner

*Primary Examiner* — Anthony Haughton
*Assistant Examiner* — Ingrid Wright

(57) ABSTRACT

A wearable device for sensing and transmitting physical activities of a user to a computing device is provided. The wearable device includes a first wristband worn around the wrist of the user, a left connecter assembly attached to the first wristband, a center assembly having sensors for sensing physical activities of the user attached to the left connecter assembly, a right connecter assembly attached to the center assembly and a second wristband worn interchangeably on the exhaustion of the primary battery inside the center assembly. The center assembly includes one or more sensors for sensing user activities. Examples of sensors include but not limited to heart rate sensor and the galvanic sensor. Further, the center assembly also includes a finger sensor to measure heart rate.

7 Claims, 6 Drawing Sheets

INTERCHANGEABLE BATTERY WEARABLE DEVICE

CROSS-REFERENCE TO RELATED APPLICATION

This application claims priority to a U.S. Provisional Application No. 61/760,737 filed on Feb. 5, 2013, the entire contents of which are incorporated herein by references in its entirety.

BACKGROUND OF THE INVENTION

1. Field of the Invention

The present invention generally relates to a wearable device for sensing user activities and more particularly relates to a wearable device for sensing user activities having means for interchanging of battery.

2. Description of Related Art

Many devices are known in the art for monitoring the physical activities of the user, such as Nike Fuelband and Jawbone Up products. Such devices usually have plurality of sensors for sensing the physical quantities of a user and then transmit the data to another computing device. Further, these devices run on a processor for continuously monitoring the activities of a user. Such devices require a battery having a long life or are rechargeable in nature. These devices are generally built-in and are non-user changeable batteries.

However, such devices lacks in providing an option of interchanging the battery for the devices. Therefore, there is a need of device wearable by a user having plurality of sensors for sensing user activities and an interchangeable battery arm. Furthermore, the wearable device should provide an option of adding other peripheral devices as per the requirement of a user.

SUMMARY OF THE INVENTION

In accordance with a preferred embodiment of the present invention, a wearable device for sensing user activities with an interchangeable battery is provided.

An object of the present invention is to provide a wearable device for sensing and transmitting physical activities of a user to a computing device. The wearable device includes a first wristband worn around the wrist of the user, a left connecter assembly attached to the first wristband, a center assembly having sensors for sensing physical activities of the user attached to the left connecter assembly, a right connecter assembly attached to the center assembly and a second wristband worn interchangeably on the exhaustion of the primary battery inside the center assembly.

The center assembly includes a bottom housing assembly positioned on the wrist of the user, one or more sensors attached on the outer surface of the bottom housing assembly for sensing user activities, a printed circuit board attached to the bottom housing assembly, a display screen attached to the printed circuit board for displaying the results of the activities sensed by the sensor, a processor connected to the printed circuit board for processing the data related to physical activities processed by the one or more sensors, a transmitter connected to the processor on the printed circuit board for transmitting the processed physical activities of the user and a primary battery connected to the printed circuit board for providing power to the display screen, the processor and the transmitter.

Another object of the present invention is to provide a lens connected to the printed circuit board for covering the display screen.

Another object of the present invention is to provide a finger sensor positioned on the top of the lens for sensing the user activities from the user's finger touch.

Another object of the present invention is to provide a top button attached on the lens for controlling the finger sensor.

Another object of the present invention is to provide a side button attached to the bottom housing assembly for controlling the one or more sensors and the finger sensor.

These and other objects, features and advantages of the invention will become more fully apparent in the following detailed description, take in conjunction with the accompanying drawings.

DETAILED DESCRIPTION OF DRAWINGS

Figure 1:
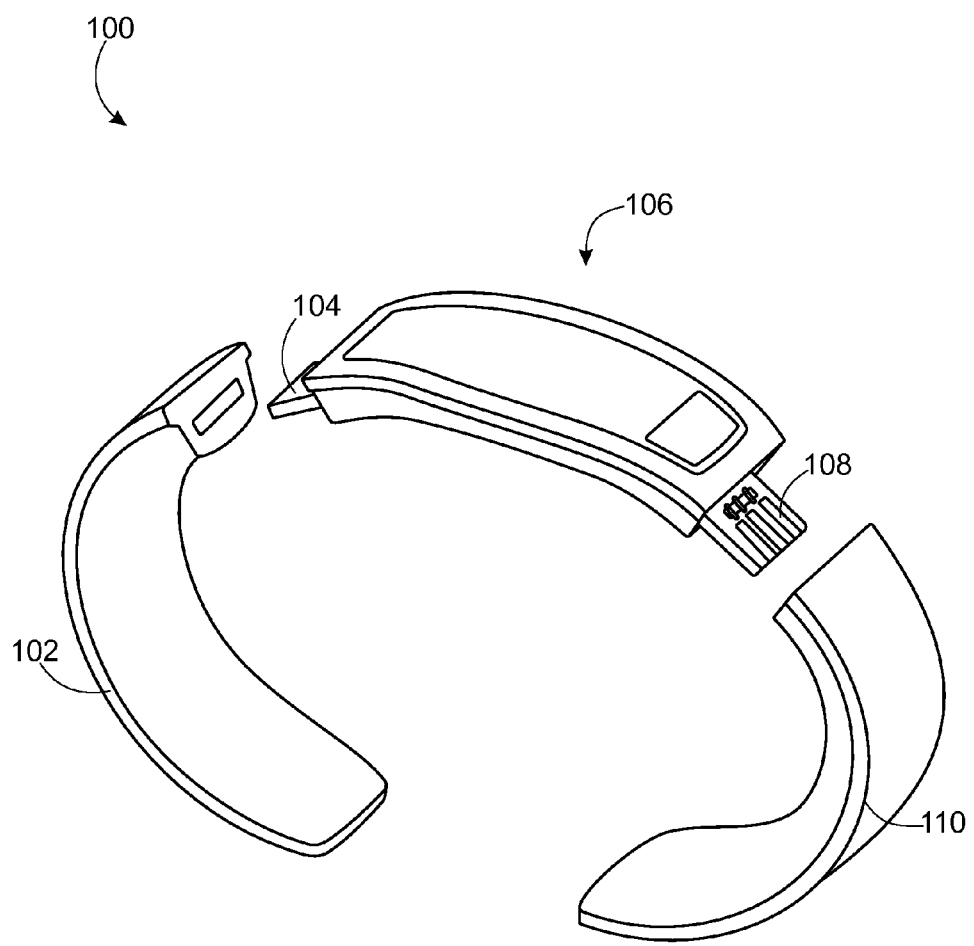
FIG. 1 illustrates a perspective view of a wearable device in accordance with a preferred embodiment of the present invention.

While this technology is illustrated and described in a preferred embodiment, a wearable device for sensing and transmitting physical activities of a user to a computing device may be produced in many different configurations, forms and computer language. There is depicted in the drawings, and will herein be described in detail, as a preferred embodiment of the invention, with the understanding that the present disclosure is to be considered as an exemplification of the principles of the invention and the associated functional specifications for its construction and is not intended to limit the invention to the embodiment illustrated. Those skilled in the art will envision many other possible variations within the scope of the technology described herein.

FIG. 1 illustrates a wearable device 100 for sensing and transmitting physical activities of a user to a computing device. The wearable device 100 includes a first wristband 102 worn around the wrist of the user, a left connecter assembly 104 attached to the first wristband 102, a center assembly for sensing and transmitting physical activities 106 connected to the left connecter assembly 104, a right connecter assembly 108 attached to the center assembly 106 and a second wristband 110 attached to the right connecter assembly 108. The first wrist band 102 is explained in detail in conjunction with FIG. 2 of the present invention. The central assembly 106 is explained in detail in conjunction with FIG. 4 of the present invention. The second wrist band 110 is explained in detail in conjunction with FIG. 6 of the present invention. The left connecter assembly 104 and the right connecter assembly 108 is explained in detail in conjunction with FIG. 3 and FIG. 5 of the present invention respectively.

Figure 2:
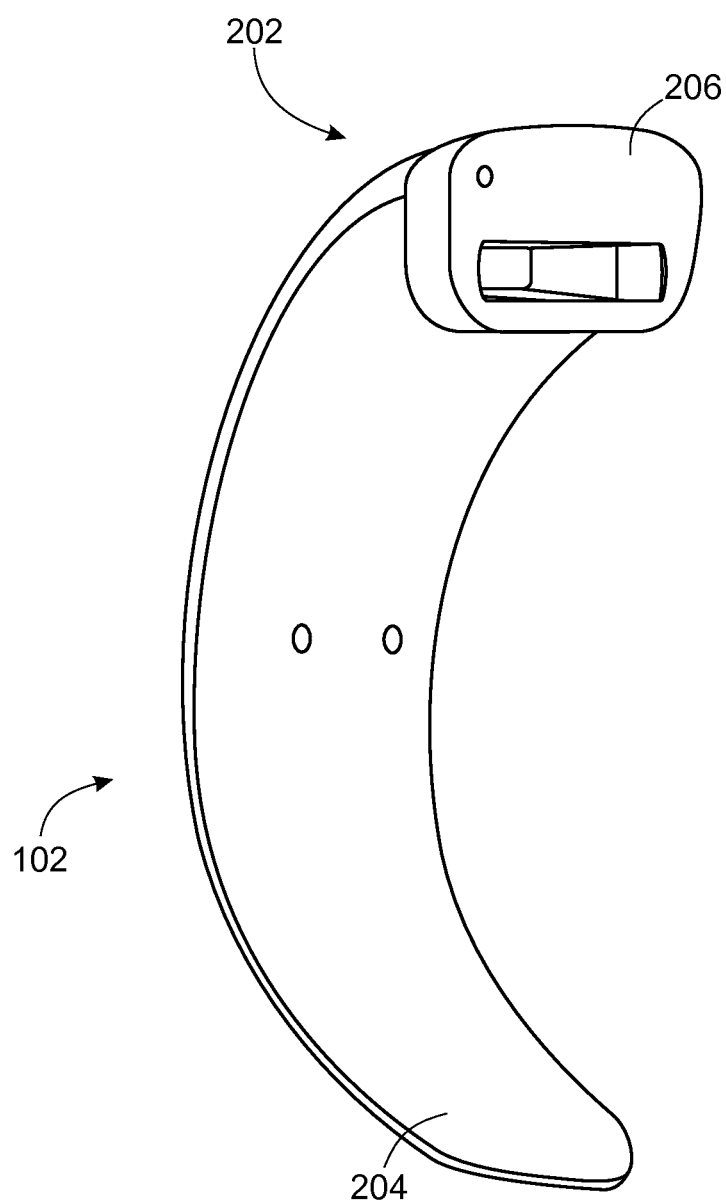
FIG. 2 illustrates a perspective view of a first wristband in accordance with a preferred embodiment of the present invention.

FIG. 2 illustrates a perspective view of the first wristband 102 in accordance with a preferred embodiment of the present invention. The first wrist band 102 worn around the wrist of the user. The first wristband 102 includes a front end 202 and a rear end 204. The front end 202 further includes a first attachment module 206 for allowing attachment of the left connecter assembly (not shown in FIG. 2). The left connecter assembly (not shown in FIG. 2) is explained in detail in conjunction with FIG. 3 of the present invention. In a preferred embodiment of the present invention, the first attachment module 206 is a female socket. The rear end 204 is curved to fit comfortably around the wrist of the user.

Figure 3:
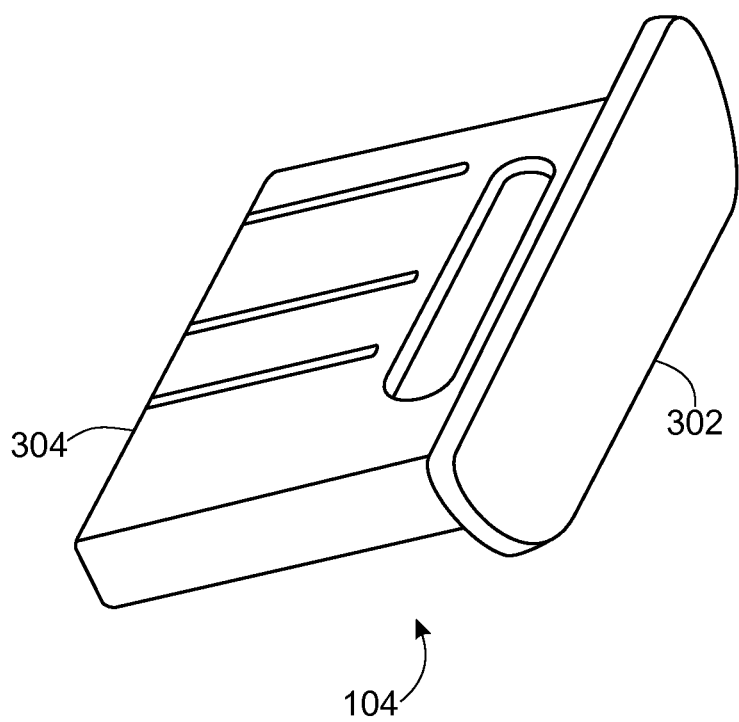
FIG. 3 illustrates an exploded view of the left connecter assembly in accordance with a preferred embodiment of the present invention.

FIG. 3 illustrates an exploded view of the left connecter assembly 104 in accordance with a preferred embodiment of the present invention. The left connecter assembly 104 includes a left first end 302 and a left second end 304. The left second end 304 is attached to the first attachment module (shown in FIG. 2 of the present invention) of the first wristband (shown in FIG. 2 of the present invention). The left first end 302 is attached to the center assembly (not shown in FIG. 3 of the present invention). The center assembly (not shown in FIG. 3 of the present invention) is explained in detailed in conjunction with FIG. 4 of the present invention. In a preferred embodiment of the present invention, the left second end 304 is a USB tongue.

Figure 4:
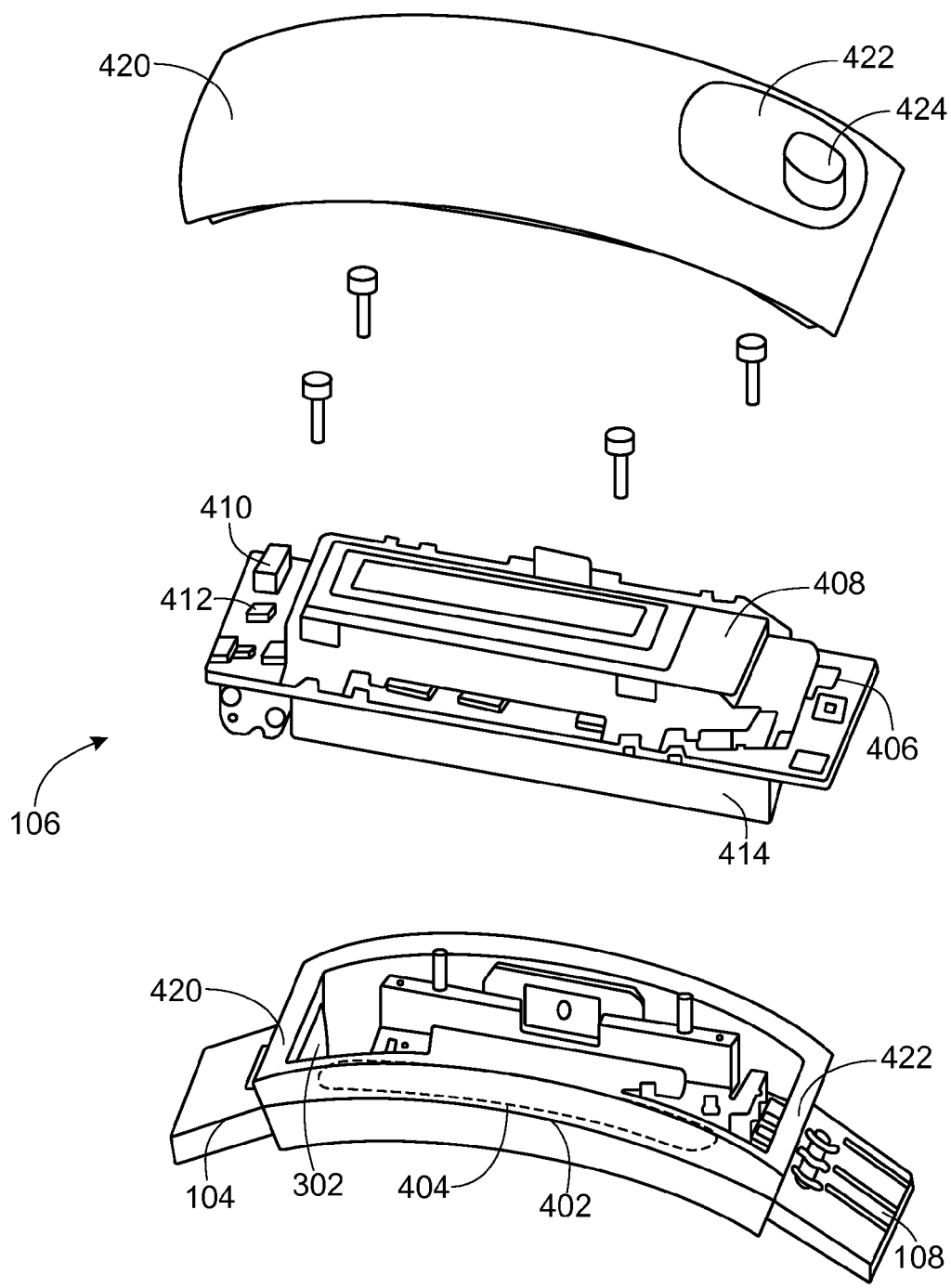
FIG. 4 illustrates an exploded view of the center assembly in accordance with a preferred embodiment of the present invention.

FIG. 4 illustrates an exploded view of the center assembly 106 in accordance with a preferred embodiment of the present invention. The central assembly 106 is connected to the left first end 302 of the left connecter assembly 104. The central assembly 106 includes a bottom housing assembly 402, one or more sensors 404, a printed circuit board 406, a display screen 408, a processor 410, a transmitter 412 and a primary battery 414.

The bottom housing assembly 402 is positioned on the wrist of the user. The bottom housing assembly 402 having a first housing end 416 connected to the left first end 302 of the left connecter assembly 104 and a second housing end 418 connected to the right connecter assembly 108. In a preferred embodiment of the present invention, shape of the bottom housing assembly 402 is elongated to allow placement on the top of the wrist of the user. However, it will readily apparent to those skilled in the art that various other shape of the bottom housing assembly 402 without deviating from the scope of the present invention.

The one or more sensors 404 are attached on the outer surface of the bottom housing 402 for sensing the physical activities of the user. The one or more sensors 404 are explained in detailed in conjunction FIG. 4 of the present invention.

The printed circuit board 406 is attached to the bottom housing assembly 402. The display screen 408 is attached on the top of the printed circuit board 406 for displaying the results of the activities sensed by the one or more sensors 404. In a preferred embodiment of the present invention the display screen 408 is an organic light emitting diode (OLED). However, it will be readily apparent to those skilled in the art that other forms of display screen 408 may also be used without deviating from the scope of the present invention. The display screen 408 is attached to the printed circuit board 406 by an adhesive layer.

The processor 410 is connected to the printed circuit board 406 for processing the data related to physical activities of the user sensed by the one or more sensors 404. Examples of processor 410 includes but not limited to 32-Bit processor, 64 Bit processor etc. However it will be readily apparent to those skilled in the art that various other forms of processor 410 may be used without deviating from the scope of the present invention.

The transmitter 412 is connected to the printed circuit board 406 for transmitting the processed physical activities of the user to the computing devices and the display screen 408. In a preferred embodiment of the present invention the transmitter 412 is a Bluetooth. However it will be readily apparent to those skilled in the art that various other forms of transmitter 412 may be used without deviating from the scope of the present invention.

The primary battery 414 is connected to the printed circuit board 406 for providing power to the display screen 408, the processor 410 and the transmitter 412. In a preferred embodiment of the present invention, the primary battery 414 is sandwiched in between the printed circuit board 406 and the bottom housing assembly 402.

In another embodiment of the present invention, the central assembly 106 further includes a lens 416 connected to the printed circuit board 406 for covering the display screen 408. Examples of material of lens 416 include but not limited to the glass or polycarbonate. However it will be readily apparent to those skilled in the art that various other materials for lens 416 may be used without deviating from the scope of the present invention.

In another embodiment of the present invention, the central assembly 106 further includes a finger sensor 418 positioned on the top of the lens 416 for sensing the user activities from the user's finger touch. The finger 418 sensor senses the physical activities of a user from finger touch. Example of the data sensed by the finger sensor 418 is the heart rate.

In another embodiment of the present invention, the central assembly 106 further includes a top button 420 attached on the lens 416 for controlling the data sensed by the finger sensor 418.

Figure 5:
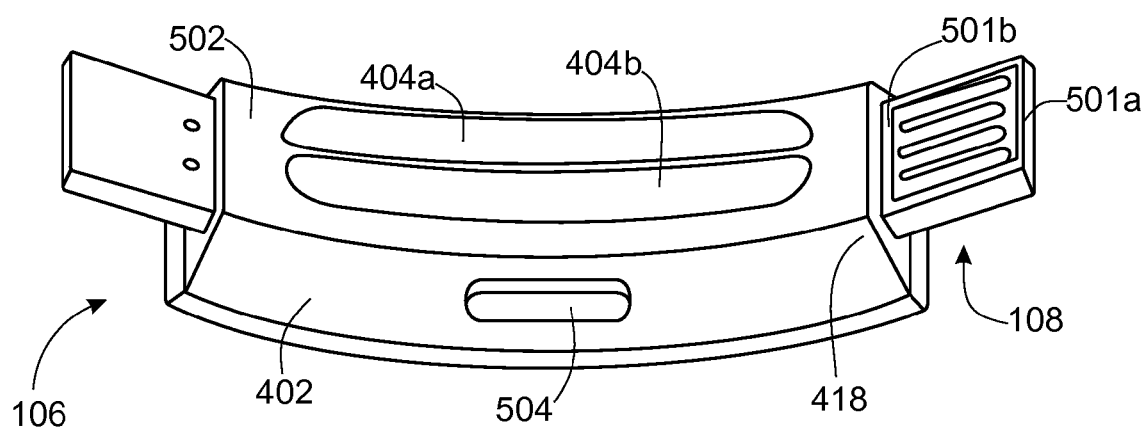
FIG. 5 illustrates a bottom perspective view of the center assembly in accordance with a preferred embodiment of the present invention.

FIG. 5 illustrates a bottom perspective view of the center assembly 106 in accordance with a preferred embodiment of the present invention. The right connecter assembly 108 includes a right first end 501a and a right second end 501b. The right second end 501b is attached to the second housing end 418 of the bottom housing assembly 402. The right connecter assembly 108 is a USB port device for allowing attachment of the second wristband (not shown in FIG. 5). The second wristband (not shown in FIG. 5) is explained in detail in conjunction with FIG. 6 of the present invention.

In a preferred embodiment of the present invention, the one or more sensors 404 such as the first sensor 404a and the second sensor 404b sensed physical activities of the user. Example of the first sensor 404a and the second sensor 404b is heart rate sensor and the galvanic sensor respectively. The one or more sensors 404 are attached on the outer surface 502 of the bottom housing 402. Thus, the one or more sensors 404 are placed on the wrist of the user.

In another embodiment of the present invention, the central assembly 106 further includes a side button 504 attached to the bottom housing 402 for controlling the one or more sensors 404 and the finger sensor (not shown in FIG. 5).

Figure 6:
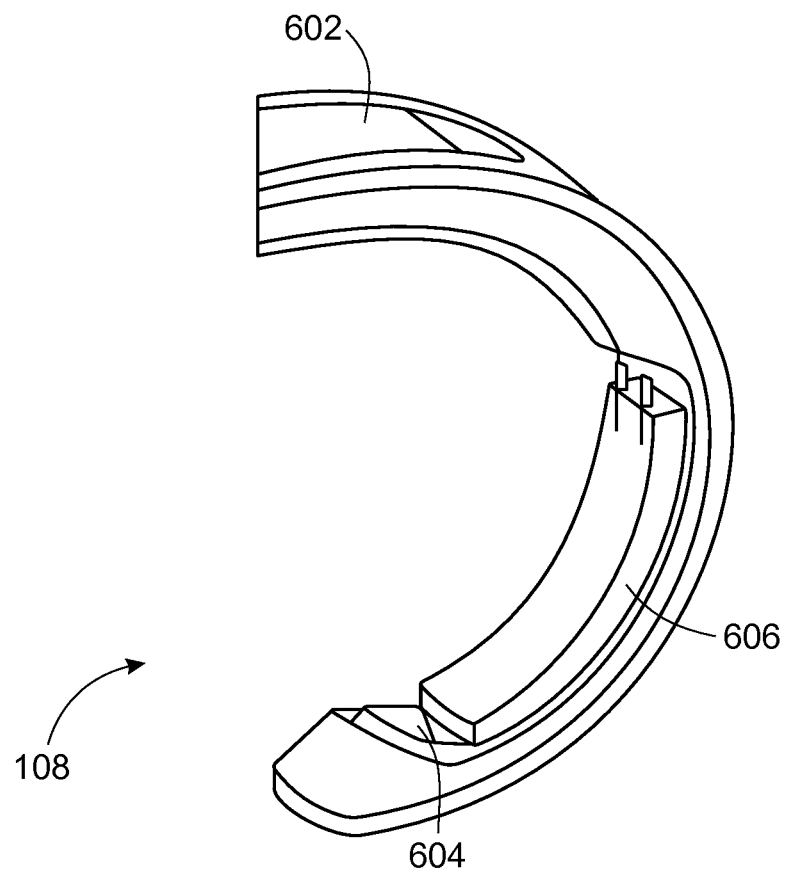
FIG. 6 illustrates a perspective view of a second wristband in accordance with a preferred embodiment of the present invention.

FIG. 6 illustrates a perspective view of the second wristband 110 in accordance with a preferred embodiment of the present invention. The second wristband 110 includes a first recess 602 for connecting to the right second end 501a and a recess 604 for placing an additional battery 606. The additional battery 606 operates on the exhaust of the primary battery (not shown in FIG. 6 of the present invention). In another preferred embodiment of the present invention, the second wristband 110 is detachable and to be placed only on the exhaust of the primary battery.

In another preferred embodiment of the present invention, the second wristband 110 further includes one or more peripheral electronic devices (not shown in FIG. 6) controlled by the processor (not shown in FIG. 6). Examples of peripheral electronic devices include but not limited to microphone, speaker, audio jack, camera, additional wireless modems (cellular modem, Wi-Fi) or additional sensors.

The present invention offers various advantages such as an additional battery source in the wristband to have alternate source of power when the primary battery source gets exhausted. Further, the device gets assemble and disassemble easily. The device includes various sensors to provide status of various physical quantities of the user with a longer battery life.

The foregoing discussion discloses and describes merely exemplary embodiments of the technology described herein. One skilled in the art will readily recognize from such discussion and from the accompanying drawings that various changes, modifications and variations can be made therein without departing from the spirit and scope of the invention.

The invention claimed is:

1. A wearable device for sensing and transmitting physical activities of a user to a computing device, said wearable device comprising: a first wristband worn around the wrist of said user, said first wristband having a front end and a rear end, wherein said front having a first attachment module and a left connector assembly and a right connector assembly, said left connector assembly having a left first end and a left second end, said left second end attached to said first attachment module of said first wristband; a center assembly connected to said left first end of said left connector assembly, said center assembly comprising: a bottom housing assembly positioned on the wrist of user, said bottom housing assembly having a first housing end and a second housing end, said first housing end connected to said left first end of said left connector assembly; one or more sensors attached on the outer surface of said bottom housing, said one or more sensors for sensing physical activities of the user; a printed circuit board attached to said bottom housing assembly; a display screen attached to said printed circuit board for displaying the results of activities sensed by said one or more sensors; a processor connected to said printed circuit board for processing the data related to physical activities sensed by said one or more sensors; a transmitter connected to said processor on said printed circuit board for transmitting said processed physical activities of said user to said computing devices and said display screen; and a primary battery connected to said printed circuit board for providing power to said display screen, said processor and said transmitter; a right connector assembly having a right first end and a right second end, said right first end attached to said second housing end of said bottom housing assembly; and a second wristband comprising second attachment module for connecting to said right second end and a recess for placing an additional battery, wherein said additional battery operates on the exhaust of said primary battery.

2. The wearable device according to claim 1 wherein said central assembly further comprising a lens connected to said printed circuit board for covering the display screen.

3. The device according to claim 1 further comprising a finger sensor positioned on the top of the lens for sensing the user activities from the user's finger touch.

4. The device according to claim 1 further comprising a top button attached on the lens for controlling the data sensed by said finger sensor.

5. The device according to claim 1 further comprising a side button attached to said bottom housing assembly for controlling said one or more sensors and said finger sensor.

6. The device according to claim 1 wherein said left second end and said right second end includes a USB port for attachment with said center assembly.

7. The device according to claim 1 said second wristband further comprising one or more peripheral electronic devices controlled by said processor.

* * * * *